United States Patent
Weilbacher et al.

[19]

[11] Patent Number: 5,931,821
[45] Date of Patent: Aug. 3, 1999

[54] CHEST DRAINAGE UNIT WITH CONTROLLED AUTOMATIC EXCESS NEGATIVITY RELIEF FEATURE

[75] Inventors: Eugene E. Weilbacher, Ellisville; David Rork Swisher, Maryland Heights, both of Mo.

[73] Assignee: Tyco Group S.a.r.l., Luxembourg, Luxembourg

[21] Appl. No.: 08/810,056

[22] Filed: Mar. 4, 1997

Related U.S. Application Data

[60] Provisional application No. 60/012,888, Mar. 5, 1996.

[51] Int. Cl.⁶ .................................................. A61M 1/00
[52] U.S. Cl. ........................ 604/321; 604/317; 604/319; 604/320
[58] Field of Search ........................... 604/4–6, 317–321, 604/405, 406; D24/108, 121; 137/205

[56] References Cited

U.S. PATENT DOCUMENTS

| | | | |
|---|---|---|---|
| 3,515,127 | 6/1970 | Reymond | 128/2 |
| 3,683,913 | 8/1972 | Kurtz et al. | 128/276 |
| 3,707,972 | 1/1973 | Villari et al. | 128/349 R |
| 3,861,390 | 1/1975 | Schachet | 604/321 |
| 3,866,608 | 2/1975 | Reynolds et al. | 128/276 |
| 3,960,165 | 6/1976 | Holbrook et al. | 137/202 |
| 4,231,366 | 11/1980 | Schael | 128/214 |
| 4,372,336 | 2/1983 | Cornell et al. | 137/205 |
| 4,455,141 | 6/1984 | Todd | 604/319 |
| 4,469,484 | 9/1984 | Kurtz et al. | 604/321 |
| 4,534,765 | 8/1985 | Todd et al. | 604/321 |
| 4,738,671 | 4/1988 | Ellicott et al. | 604/319 |
| 4,744,785 | 5/1988 | Rosenthal et al. | 604/4 |
| 4,781,707 | 11/1988 | Boehringer et al. | 604/317 |
| 4,798,578 | 1/1989 | Ranford | 604/4 |
| 4,857,042 | 8/1989 | Schneider | 604/4 |
| 4,911,697 | 3/1990 | Kerwin | 604/318 |
| 4,923,451 | 5/1990 | McCormick | 604/321 |
| 4,988,342 | 1/1991 | Herweck et al. | 604/321 |
| 5,026,358 | 6/1991 | Everett, Jr. et al. | 604/320 |
| 5,055,198 | 10/1991 | Shettigar | 210/650 |
| 5,114,416 | 5/1992 | Karwoski et al. | 604/321 |
| 5,141,504 | 8/1992 | Herweck et al. | 604/317 |
| 5,184,652 | 2/1993 | Fan | 141/21 |
| 5,286,262 | 2/1994 | Herweck et al. | 604/321 |
| 5,372,593 | 12/1994 | Boehringer et al. | 609/319 |
| 5,380,314 | 1/1995 | Herweck et al. | 604/403 |
| 5,507,734 | 4/1996 | Everett, Jr. et al. | 604/320 |

*Primary Examiner*—John G. Weiss
*Assistant Examiner*—David J. Cho
*Attorney, Agent, or Firm*—Ronald W. Alice

[57] ABSTRACT

The present invention provides for an improved air-flow sensitive float valve interposed between the collection chamber and one arm of the water seal chamber for allowing the patient to draw as much vacuum pressure as is required during deep inspiration. The float valve also functions to provide for an automatic controlled release of excess negative pressure in the collection chamber during either continuous autotransfusion or when there is a low air flow rate condition present. By tailoring a specific amount of water to a given size chamber, the water column inside the water seal chamber is allowed to momentarily engage the floating mechanism before the water seal chamber is emptied of water and a column of air is subsequently forced through the water column towards the momentarily sealed valve. Once the air column reaches the valve, the water supporting the valve is displaced and the valve is released until the air column is replaced by another rising water column. This displacement of air through the water column causes the valve to "shuttle" between open and closed positions as the alternating rising water and air pocket engages the valve so that sub-atmospheric pressure in the collection chamber is maintained and excess negative pressure is relieved.

40 Claims, 4 Drawing Sheets

5,931,821

CHEST DRAINAGE UNIT WITH CONTROLLED AUTOMATIC EXCESS NEGATIVITY RELIEF FEATURE

This application claims priority from Provisional Application No. 60/012,888 filed Mar. 5, 1996.

BACKGROUND TO THE INVENTION

1. Field of the Invention

The present invention relates to a system for draining fluids from the body cavity of a patient, and more specifically to an apparatus for automatically regulating negative pressure in the collection chamber of the system during operation to prevent exposing the patient to dangerously high negative pressure levels. More particularly, this invention relates to an air flow sensitive, buoyant valve that closes when a patient generates the required high air flow rate in the system because of a patient's inspiration, or it shuttles between open and closed positions when a low air flow rate generates excess negative pressure inside the collection chamber.

2. Prior Art

A chest drainage unit is an apparatus for suctioning gases and liquids from the pleural cavity of patients. The pleural cavity lies within the rib cage above the diaphragm and is surrounded by the pleural membrane. The pleural cavity contains both lungs, which in their normal expanded state fill the pleural cavity. Several conditions and diseases such as interventional surgery, trauma, emphysema and various infections can cause a build up of liquid and gases around the lungs in the intrapleural space. When this happens, it causes the lungs to collapse to a volume much less than that of the pleural cavity, thereby severely impairing breathing functions of the patient. The lungs can be re-expanded to their normal state to fill the pleural cavity by draining the liquid and gases from the intrapleural space using a chest drainage unit.

Chest drainage units are also used during autotransfusion for recovering autologous blood from the patient's pleural and mediastinal cavities and transfusing that blood back into the patient. Autotransfusion offers significant advantages over normal transfusion procedures which use homologous blood from other humans. Autologous blood reduces the risk of adverse reactions and transmission of infectious disease while supplying a readily available and safe source of compatible blood to the patient. For these reasons, chest drainage units are being designed to both evacuate fluids from the intrapleural space and autotransfuse shed autologous blood back into the patient.

Various devices have been developed to drain and collect fluids such as blood from the intrapleural space for subsequent autotransfusion. U.S. Pat. No. 4,857,042 to Schneider illustrates the prior art development of autotransfusion chest drainage units. The device includes a collection chamber for the collection of fluid from the pleural cavity, a water seal chamber for preventing passage of gas from the atmosphere into the patient's pleural and mediastinal cavities, and a manometer chamber for regulating the degree of vacuum in the system. An inlet port of the collection chamber is connected to the patient's pleural cavity via a thoracotomy tube that deposits shed blood and gases into the collection chamber. The device is also connected to a blood compatible pump at an outlet port of the collection chamber for pumping autologous blood back into the patient. The Schneider device is also provided with a valve mechanism above the water seal chamber to permit the passage of fluids from the water seal chamber in the event of a sudden increase in negative pressure inside the collection chamber, such as when the patient inhales, or blood is withdrawn from the collection chamber with a blood pump or other similar device.

One drawback with the Schneider device is that no provision is made for autotransfusing simultaneously with draining the pleural cavity. Prior art drainage devices generally could not be used to simultaneously collect blood from the pleural and mediastinal cavities and autotransfuse, because there was no provision for automatic regulation of negative pressure during autotransfusion. During continuous autotransfusion, as fluid exits the collection chamber, the remaining fluid volume falls and pressure level concurrently drops within the collection chamber and pleural cavity. It is therefore vital that negative pressure within the collection chamber be maintained within a relatively narrow range to keep bleeding to a minimum and prevent any damage to the intrathoracic tissue which might occur. It is also important to maintain negative pressure within a relatively narrow range in order to prevent water from being transferred out of the water seal chamber and into the collection chamber due to loss of vacuum therein. Permanent loss of water in this manner would render the water seal useless as a one way valve for gases passing out of the collection chamber.

One approach in solving this problem is to provide a collapsible bag whose volume can change as required. U.S. Pat. No. 4,443,220 to Hauer et al. discloses such a bag which may be removed from the drainage device when full and placed on a stand to effect reinfusion, however this type of device is incapable of simultaneous drainage and reinfusion. Another method is illustrated by U.S. Pat. No. 4,548,413 to Russo wherein a mechanical pressure regulating mechanism in communication with the collection chamber is provided which regulates the sub-atmospheric pressure in the collection chamber independent of the chamber's effective volume. Unfortunately, such regulating mechanisms are costly and often unreliable.

A further problem also arises with the drainage tube which connects the patient to the drainage device. The drainage tube from a patient may itself cause a significant increase in negative pressure in the collection chamber when a nurse attempts to clear or "strip" away any occlusions blocking the tube. "Stripping" is where a nurse or practitioner clears the tube's passageway of blockages that occlude the tube by pinching off a portion of the tube nearest the patient, moving the pinch along the tubing towards the inlet port of the CDU, and then releasing the pinch. This "stripping" action forces any blockages along the tube, but also introduces substantial fluctuations in pressure inside the drainage device due to the sudden release of low pressure in the tube after the pinch is released.

Prior art drainage devices are also designed to permit a patient to draw as much vacuum pressure as is required for both normal and deep inspiration without transferring water from the water seal chamber into the collection chamber. Prior art devices have included push button type valves in communication with the collection chamber for manually venting excess negative pressure inside the drainage device. However, problems exist with manual venting.

One problem associated with manual venting of excess negative pressure is that known venting systems do not give an inherent indication that a high vacuum is present in the collection chamber. Another problem associated with manual venting of excess vacuum is that the nurse must manually push down on the push button valve in order to allow atmospheric air to vent inside the collection chamber. Such a procedure can take upwards of a full minute and requires the nurse to apply constant pressure on the push button valve during release. Further, the nurse must carefully observe and coordinate the level of the water seal with the release of vacuum on the push button valve. Without careful observation and coordination of the manual pressure release during gravity drainage of the collection chamber, the patient's intrathoracic vacuum could be lowered to dangerously low level, such as atmospheric pressure, and cause a serious clinical event to the patient known as a pneumothorax.

One approach to the solution of venting excess negative pressure from the drainage device is illustrated in U.S. Pat. No. 5,114,416 to Karwoski et al. The Karwoski et al. device discloses a float valve mechanism interposed between the water seal chamber and the collection chamber that provides for automatic controlled release of excess vacuum beyond that required for patient inspiration. The Karwoski et al float valve allows the patient to draw high vacuum in the collection chamber for breathing while automatically releasing negative pressure when excessive vacuum is maintained for an extended period of time therein. The float valve includes a valve seat forming an aperture and buoyant ball that is adapted to seal against the aperture of the valve seat. During periods when high vacuum exists in the collection chamber due to patient inspiration or deep gasp exercises, water from the water seal chamber rises until it lifts and seats the ball against the valve seat. Once the ball is engaged, the aperture is shaped to permit the water to still pass therethrough but at a substantially reduced rate.

During periods of extended high, excessive vacuum in the collection chamber the water column becomes depleted as enough water is forced up one arm of the water seal chamber and passes through the aperture. Once through the aperture, the water flows into an overflow chamber and the height of the water column below becomes insufficient to maintain the ball valve in the seated position due to leakage of ambient air into the collection chamber following the final influx of water therethrough, thereby effecting automatic release of the valve. However, the Karwoski et al. device suffers from several drawbacks.

The Karwoski et al. floating valve is activated by hydraulic pressure of the water column from the water seal lifting and engaging the valve ball into the sealed position. Unfortunately, the design of the Karwoski et al. valve permits leakage of fluid when engaged in the sealed position. This leakage eventually allows air to flow into the collection chamber during extended deep gasp exercises and effectively lowers the negative pressure therein over time, thus making it difficult for the patient to maintain a constant negative pressure inside the collection chamber during the deep gasp exercise. During convalescence, it is preferable to maintain a constant negative pressure inside the pleural cavity in order to allow the patient to effectively exercise the diaphragm muscles under the cavity. Without a sufficient negative pressure, the diaphragm muscles are unable to exert enough muscular action against the pleural cavity due to the underinflated condition of the lungs.

The Karwoski et al. device also suffers from other drawbacks. Although this device provides automatic negative pressure relief during low flow situations like continuous autotransfusion, the valve is not designed to be air-flow sensitive and is incapable of maintaining excessive vacuum when the patient is performing extended deep gasp exercises. Often during convalescence of the pleural cavity, patients are required to perform deep gasp exercises in order to strengthen the diaphragm muscles beneath the lungs. In performing these exercises a sudden and high excessive vacuum is generated in the collection chamber when the patient takes a sudden and deep inspiration. When using the Karwoski et al. device, the patient is incapable of maintaining the required high vacuum inside the pleural cavity during an extended deep gasp exercise because the float valve does not remain closed. Instead, the valve leaks water after the water column from the water seal chamber engages and seals the float valve, and air continues to leak past the valve after the water is depleted. Thus, the Karwoski's float valve operates only when the water column is drawn upward and engages the valve into its sealed position, and the valve will always leak air even after the water column under it is depleted.

Accordingly, it is the principal object of the present invention to provide a fluid recovery system having an improved flow-sensitive, buoyant valve that provides for automatic and/or complete closure when a minimum amount of air flow is applied thereto.

Another important object of the present invention is to provide an air-flow sensitive valve that maintains substantially the same negative pressure inside the collection chamber of the apparatus as is being maintained in the patient's pleural cavity while the patient is performing deep gasp exercises.

It is also an object of the present invention is to provide an improved float valve that does not leak during operation.

Another further object of the present invention is to provide a buoyant valve that can operate to relieve excess negative pressure when there is a slow rate of increase in negative pressure within the apparatus.

It is a further object of the present invention to provide a buoyant valve that will shuttle between open and closed positions in such a manner that excess negative pressure is automatically relieved when there is a slow rate of increase in negative pressure.

Another object of the present invention is to provide a valve that combines the dual functions of relieving excess negative pressure during low flow rate conditions while maintaining equilibration of the collection chamber and pleural cavity pressures during high air flow rate conditions.

SUMMARY OF THE INVENTION

The present invention provides for a disposable unitary structure for sterile collection of fluids from the pleural cavity of a patient, and if desired, for simultaneously reinfusing such fluids back to the circulatory system of the patient. The apparatus comprises a rigid collection chamber for receiving fluids drained from the pleural cavity, a U-shaped water seal chamber for preventing passage of atmospheric air into the collection chamber, and a manometer chamber for regulating the amount of vacuum inside the collection chamber. In the preferred embodiment, the collection chamber has three ports: the first port is adapted for connection to a thoracotomy tube for draining fluids from the pleural and mediastinal cavities into the collection chamber; the second port communicates with the water seal chamber; and the third port is adapted for connection with an infusion pump and separate collection vessel for delivery and reinfusion of collected fluids back into the circulatory system of the patient.

The apparatus is configured to operably maintain a selected negative pressure range in the collection chamber during the outflow of collected fluid, and to permit reinfusion of collected blood from the collection chamber simultaneously with drainage from the pleural or other body cavity into the same chamber. Alternatively, the apparatus may be used as a means of facilitating patient convalescence. This is accomplished by maintaining a substantially constant negative pressure condition inside the collection chamber when the patient exercises the diaphragm muscles through deep extended gasp exercises during convalescence.

The present invention also includes an improved air-flow sensitive float valve interposed between the collection chamber and one arm of the water seal chamber for allowing the patient to draw as much vacuum pressure as is required during deep inspiration. The float valve also functions to provide for an automatic controlled release of excess negative pressure in the collection chamber during either continuous autotransfusion or when there is a low air flow rate condition present. By tailoring a specific amount of water to a given size chamber, the water column inside the water seal chamber is allowed to momentarily engage the floating mechanism before the water seal chamber is emptied of water and a column of air is subsequently forced through the water column towards the momentarily sealed valve. Once the air column reaches the valve, the water supporting the valve is displaced and the valve is released until the air column is replaced by another rising water column. This displacement of air through the water column causes the valve to "shuttle" between open and closed states as the alternating rising water and air pocket engages the valve so that sub-atmospheric pressure in the collection chamber is maintained and excess negative pressure is relieved.

In another mode, the valve has an air flow-sensitive feature that permits activation of the valve during high air flow conditions without the valve having to be engaged by the column of water required in the Karwoski et al system. When a patient takes a sudden and deep inspiration, a pocket of air normally precedes the rising water column up the one arm of the water seal chamber towards the collection chamber. The air-sensitive valve of the present invention is designed with a valve body that is sensitive to air flow and is designed to lift the valve towards a sealing engagement with the sealing member when the air column reaches the valve chamber.

This valve design automatically restores the patient back to minimum lower vacuum threshold and provides a simple system of automatic release of excess negative pressure that does not leak fluid nor require any monitoring by an operator when the chest drainage unit is operating under continuous autotransfusion. In addition, the valve design permits more effective convalescence of the patient during chest drainage due to the air-flow sensitive valve feature that closes during high air-flow conditions when a rising air column caused by the patient performing deep gasp exercises engages the valve.

DETAILED DESCRIPTION OF THE PREFERRED EMBODIMENT

Figure 1:
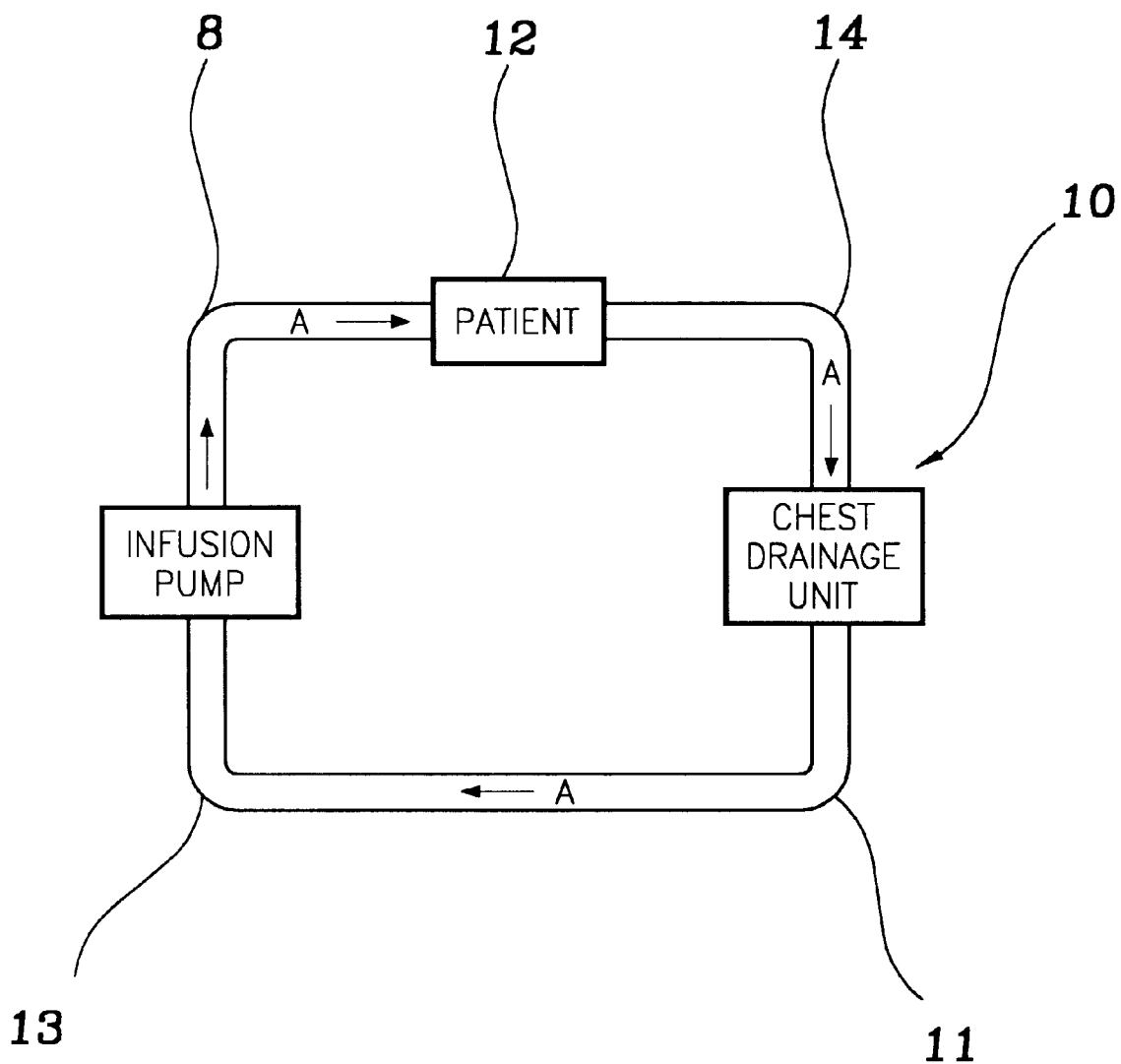
FIG. 1 is a simplified block diagram showing the basic operation of a prior art autotransfusion system.

A prior art autotransfusion system in accordance with the present invention is shown in FIG. 1. The basic configuration of an autotransfusion system 10 comprises a chest drainage unit (CDU) 11 for sterile collection and if desired, transfer of shed fluids from a patient 12, a blood compatible infusion pump 13 connected to the CDU 11 for reinfusing shed blood back to the patient 12, and infusion tubing 14 for use as a conduit to transfer the blood between the autotransfusion system 10 and the patient 12. Liquid flow A denotes the direction of the fluid flow within system 10.

The basic operation of the autotransfusion system 10 is disclosed in U.S. Pat. No. 4,798,578 to Ranford and is herein incorporated by reference in its entirety. In short summary, the autotransfusion system 10 operates by using CDU 11 for the sterile collection of blood and fluids drawn from patient 12, and simultaneous reinfuses the fluids back to the circulatory system of patient 12.

The general process of transfusing a patient's blood begins by drawing fluids from the patient's pleural cavity using a suction source (not shown) located at CDU 11 to create a positive liquid flow A through the autotransfusion system 10. The suction forces shed body fluids from patient 12 through infusion tubing 14 and into the collection chamber (not shown) of CDU 11. As fluid enters the collection chamber 15 at collection port 18, it is run through a gross filter (not shown) which traps macroscopic debris such as blood clots, bone fragments and the like that become entrained in blood or other body fluids. Once the fluid is filtered, it is temporarily stored in the collection chamber 15 where it is again filtered using a microaggregate filter (not shown) as the fluid exits the CDU 11. In alternative embodiments, the egress of blood from the collection chamber 15 can be from any suitable site along the surface of the collection chamber where the infusion tubing 14 may be attached. Once the blood is filtered through the filter, it goes to infusion pump 13 where the blood is reinfused back to patient 12 through infusion tubing 14, thereby finishing one complete autotransfusion cycle. Infusion tubing 14 may be made of any suitable flexible plastic material, for example polyurethane or PVC, for use in transmitting fluids and gas throughout system 10.

Figure 2:
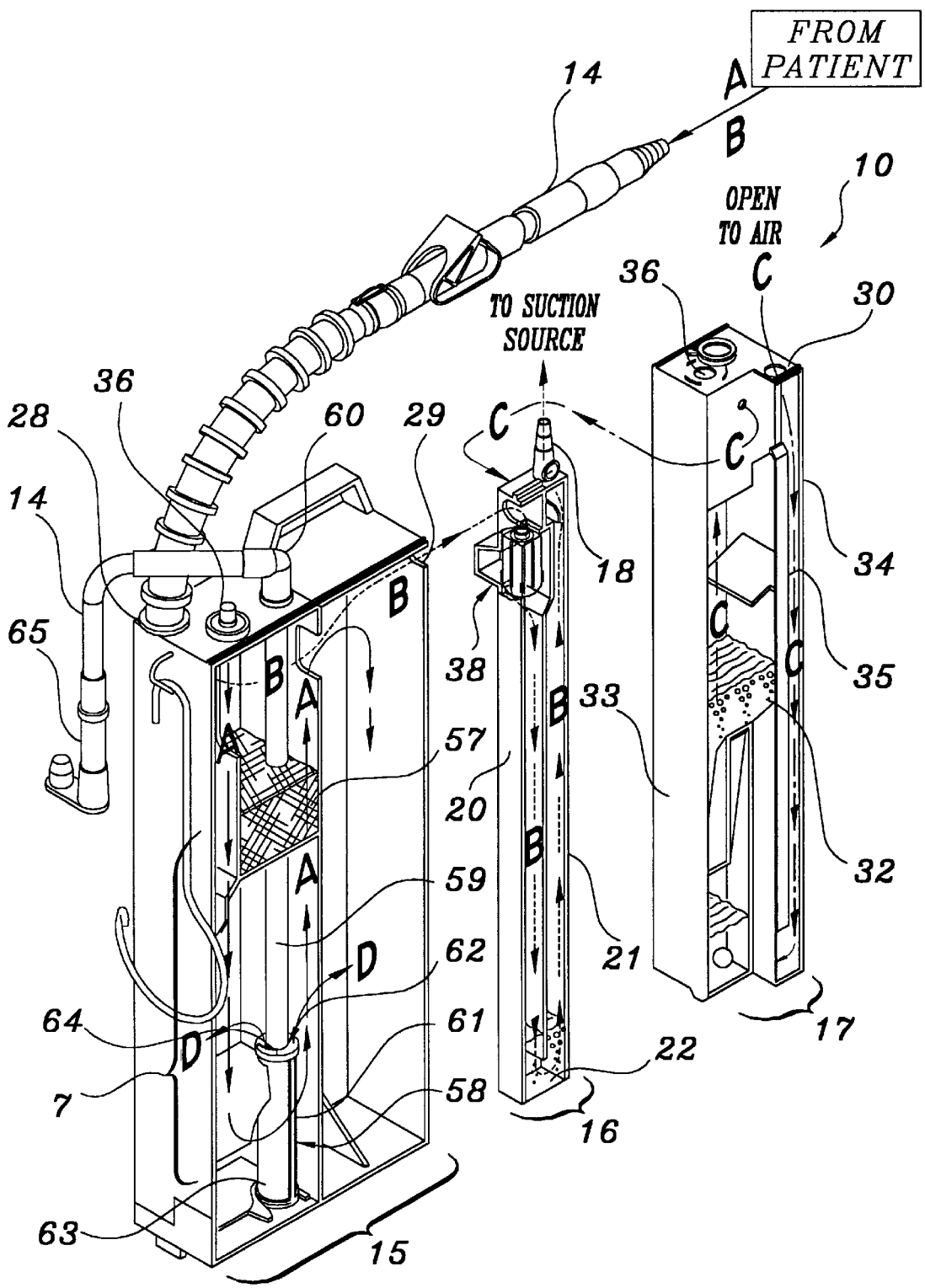
FIG. 2 is a partial cross section showing an exploded view of an autotransfusion chest drainage unit in accordance with the present invention.

Referring to FIG. 2, the operative features of CDU 11 in accordance with the present invention will be discussed in greater detail. An autotransfusion CDU 11 consists of a standard three chamber unit found in the prior art comprising a blood collection chamber 15, a water seal chamber 16 and suction control chamber 17. The blood collection chamber 15 is designed to receive fluid drained from the patient's pleural and mediastinal space, but it may also function as a filtration site to filter blood and other fluids of unwanted debris. In an alternative embodiment, CDU 11 may be configured to have an additional second collection chamber (not shown) separate from the CDU 11 body which acts as the filtration site while the collection chamber 15 inside CDU 11 acts as an overflow chamber for the second detached chamber, as disclosed in the aforementioned Ranford patent.

The other two chambers, the water seal chamber 16 and suction control chamber 17, serve to control and regulate the liquid flow A inside the collection chamber 15 as well as the pressure inside CDU 11. The suction control chamber 17 provides regulation of negative pressure during operation. Negative pressure within the CDU 11 is controlled by the height of water 32 in the suction control chamber 17 which insures a continuous suction of the pleural cavity and also alleviates concerns over possible tissue invagination in the thoracic catheter during high levels of negative pressure within the cavity.

As further shown in FIG. 2, the suction control chamber 17 consists of a U-shaped chamber having first and second arms 33, 34 respectively. A column of water 32 fills the bottom portion of the suction control chamber 17 and extends upward through both arms 33, 34. First arm 33 is in communication with both a second arm 21 of the water seal chamber 16 and a suction source (not shown) while the second arm 34 is open to atmospheric air which maintains an area of atmospheric pressure inside the arm 34 above the water line 35. Air flow C denotes the air flow throughout the suction control chamber 17. Air flow C shows atmospheric air being pulled into the second arm 34 through open port 30 and into first arm 33 where it exits arm 33 through the suction port 18 towards the suction source. The height of the column of water 32 interposed between the first arm 33 exposed to vacuum source pressure and the second arm 34 which is at atmospheric pressure determines the level of negative pressure inside the collection chamber 15 and water seal chamber 16. For example, 20 cm of water 32 at the column translates to a negative pressure of −20 cm inside the collection chamber 15. U.S. Pat. No. 4,439,190 to Protzmann et al. gives a more detailed description of a typical suction control chamber of a CDU 11 and its operation is herein incorporated by reference.

The water seal chamber 16 prevents reflux of air and fluid back to the patient by preventing the reentry of air and fluid into the collection chamber 15 using an air sensitive, buoyant valve 38 in combination with a water seal 22. As shown in FIG. 2, the air flow B is created by applying the source of suction to suction port 18 located at the top of the water seal chamber 16. The applied suction creates an air flow B that forces fluid from the patient's body (not shown) through the infusion tubing 14 and into the top of the collection chamber 15 at port 28 where air flow B passes through opening 29 and into the water seal chamber 16. Once inside the water seal chamber 16, air flow B travels down a first arm 20 and through the water seal 22 located at the bottom portion of chamber 16. After passing through the water seal 22, air flow B travels up second arm 21 where it exits at suction port 18. Thus, air flow B creates a positive flow path that forces gases out of collection chamber 15 and through water seal 22 where these gases are removed from CDU 11 through suction port 18.

The first arm 20 of the water seal chamber 16 is in fluid flow communication with second arm 21 through water seal 22 at one end and the collection chamber 15 at the other end, while the second arm 21 is in fluid flow communication with the first arm 20 at one end and the suction control chamber 17 at its other end respectively. Water seal 22 functions as a protective one way valve that allows air to escape from the collection chamber 15, while preventing contaminated atmospheric air from reentering the pleural cavity of the patient. By interposing a water seal 22 at the bottom portions of both first and second arms 20, 21, fluid is prevented from passing back through the water seal 22 due to the difference in pressure maintained between the two arms 20, 21, thus preventing a reflux action. The importance in preventing reflux is that under certain respiratory conditions, a sudden increase in pressure within the pleural cavity can appear. For example, an air leak in the pleural cavity can interfere with the normal respiratory function of the patient's lungs. Finally, the bubbling action shown in the water seal 22 represents evacuated air from the collection chamber 15 that has passed through seal 22 into second arm 21.

Figure 3:
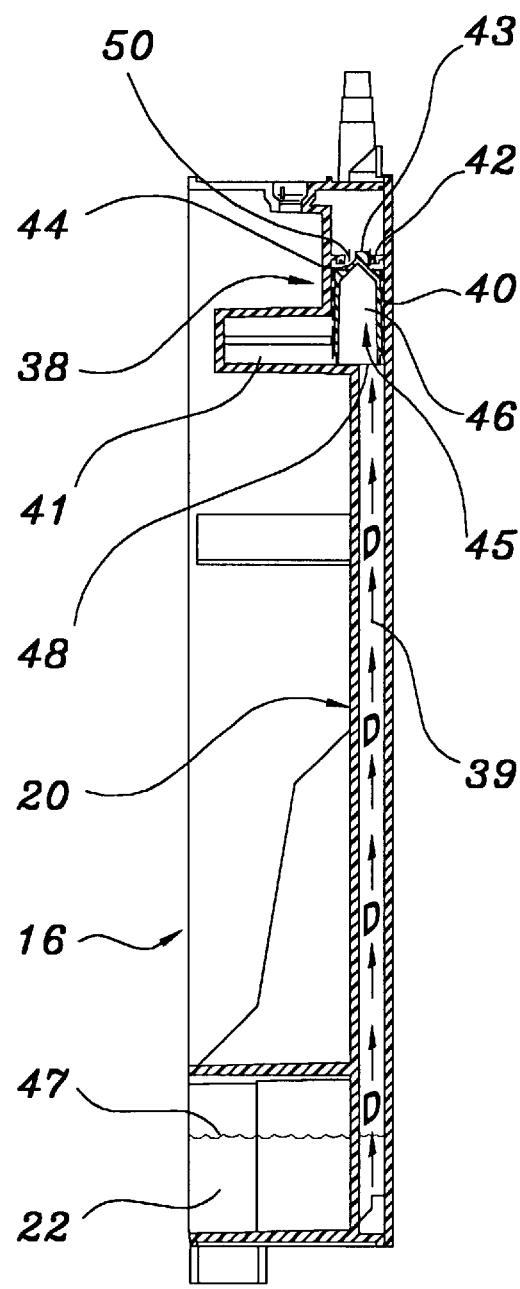
FIG. 3 is a partial cross section of the water seal chamber showing the operation of the valve in accordance with the present invention.

In addition to water seal 22, which prevents any reflux of gases back into the collection chamber 15, an air flow sensitive, buoyant valve 38 is provided at the top portion of water seal chamber 16 as a further safeguard. Referring to FIG. 3, valve 38 is positioned at the top portion of column 39 of water seal chamber 16 which includes a valve chamber 40 and accumulation chamber 41. The top portion of valve chamber 40 defines a valve seat 42 which forms an aperture 50 therethrough and is shaped for air-tight engagement with valve 38 when valve 38 is seated therein. CDU 11 is also designed so that air can escape through an automatic positive pressure relief valve 36 when an overpressure condition occurs inside the patient's pleural cavity, e.g. when the patient coughs. The automatic positive relief valve 36 is positioned on the top portion of CDU 11 and is in fluid flow communication with the suction control chamber 15. Similarly, the collection chamber 15 has a negative pressure relief valve 37 which manually vents excess negative pressure from the patient's pleural cavity when actuated by a nurse.

In addition to air flow B, there exists an air flow C which is ambient or atmospheric air that enters the CDU 11 through open port 30 and forced through the suction control chamber 17 and into the top portion of the water seal chamber 16 where air flow C exits through suction port 18.

During an overpressure condition in collection chamber 15, accumulation chamber 41 functions to hold excess water that rises up the column 39 and also serves as a platform for holding valve 38 in place when the valve 38 is disengaged from valve seat 42.

Figure 4:
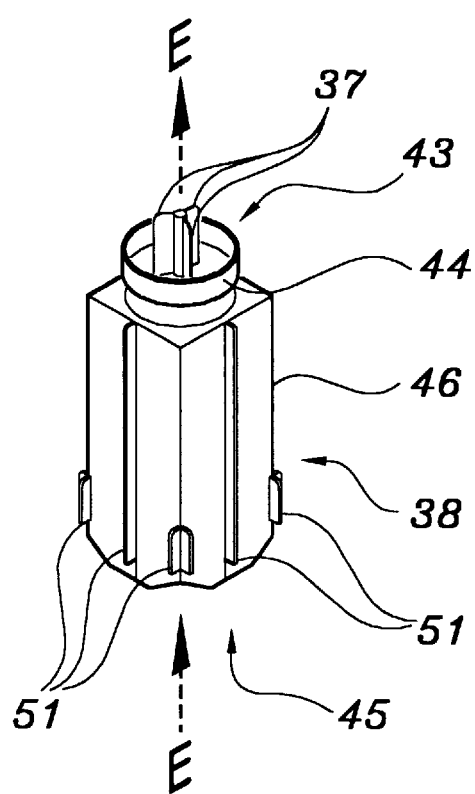
FIG. 4 is a perspective of the valve in accordance with the present invention.

With reference to FIG. 4, a more detailed description of valve 38 will be discussed. Valve 38 has a rectangular hollow-shaped configuration that comprises a valve body 46 and a separate grommet 44 adapted to fit over the guide 43. In the preferred embodiment, the valve body 46 has a top portion that forms a guide 43 and four side walls that form an interior chamber 45 therein. Interior chamber 45 is designed to be air flow sensitive and allows the valve 38 to be lifted upward into sealing engagement with the valve seat 42 when either a sudden reflux of air in the direction of air flow E occurs or a slow rise in the water seal 22 lifts and engages valve 38 which causes an excessive negative pressure condition in the collection chamber 15. Although the valve 38 has a rectangular shape, any suitable shape design having the aforementioned aerodynamic properties is felt to fall within the spirit and scope of the present invention.

Figure 5:
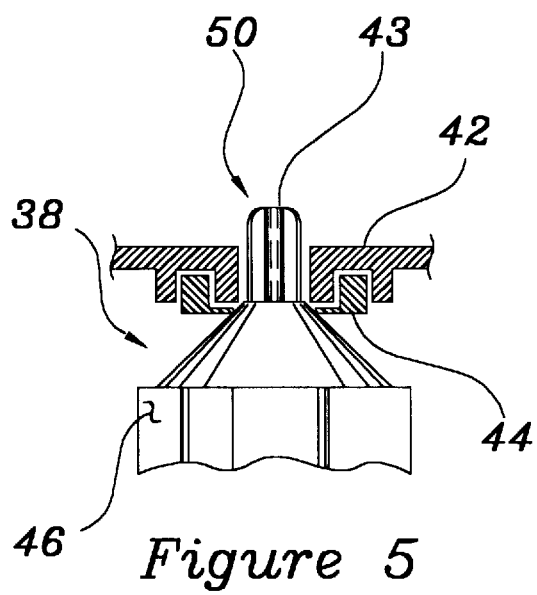
FIG. 5 is a partial cross section showing the sealing engagement of the valve to the valve seat in accordance with present invention.

With reference to FIG. 5, valve 38 is provided with grommet 44 for sealing the valve 38 against the valve seat 42 in fluid-tight engagement therein. Preferably, the grommet 44 has a ring shape design that fits over the guide 43 and is interposed between the valve body 46 and the valve seat 42 in such a manner that the grommet 44 effectively seals the aperture 50 from fluid flow communication therethrough when the valve 38 is engaged therein. The grommet 44 may be made of any suitable flexible plastic material, for example polyurethane or silicone, that effectively seals the valve 38 against the valve seat 42 from fluid flow communication when engaged.

Referring back to FIG. 4, guide 43 is provided with a plurality of fins 37 that facilitate guide 43 through the aperture 50 when valve 38 is being seated against valve seat 42. To further enhance the aerodynamic design of valve 38, a plurality of flanges 51 are also provided at each bottom corner and side wall of valve 38 for influencing the air flow through valve chamber 40 and around valve 38.

With reference to FIG. 3, a detailed description of the operation of valve 38 will be discussed. Valve 38 operates in two modes: (1) during low air flow rate conditions in which excessive negative pressure increases at a relatively gradual rate, such as during autotransfusion, valve 38 prevents entry of rising water from the water seal 22 from entering the collection chamber 15; and (2) during high air flow conditions in which excessive negative pressure builds up at nearly an instantaneous rate, such as when a patient takes a rapid deep inspiration or "gasp", valve 38 prevents ambient or atmospheric air from the water seal chamber 16 from entering the collection chamber 15.

In the first mode, valve 38 operates to prevent the ingress of water from the water seal 22 into the collection chamber 15. During autotransfusion an excess negative pressure slowly builds up in the patient's pleural cavity which gradually forces water within water seal 22 to rise up column 39 until it engages valve 38. This forced rising of water is due to the pressure differential between the collection chamber 15 and the second arm 21 of the water seal chamber 16 and is generated by operation of infusion pump 13. First water level 47 denotes the original water level in water seal 22 before autotransfusion process draws water up column 39, while flow path D denotes the direction of the rising water. When autotransfusion begins, the low air flow rate condition will cause the water level to slowly rise up column 39 from its first water level 47 until it reaches a second water level 48 and engages valve 38. Once valve 38 is engaged, the further rising water will begin filling both the accumulation chamber 41 and interior chamber 45 and valve 38 will begin to rise up the valve chamber 40 until valve 38 is fully seated against the valve seat 42, thereby preventing fluid flow communication therethrough.

After valve 38 has seated itself against valve seat 42 in response to the low air flow rate condition caused by autotransfusion, the water seal chamber 16 of the present invention is specifically configured to permit "shuttling" of valve 38 during the remainder of the autotransfusion procedure. In this manner, further excess negative pressure is not allowed to build up in collection chamber 15. Shuttling as described herein is the up and down motion of valve 38 as it shuttles between closed and open positions in response to this slow increase in excess negative pressure generated by infusion pump 13. Although shuttling is described as an up and down motion of valve 38, any back and forth action that closes and opens valve 38 is felt to fall within the scope of the present invention. Shuttling prevents the accumulation of excess negative pressure in the collection chamber 15 after valve 38 has been initially closed by the rise of the water in column 39. By allowing small amounts of ambient air to pass into chamber 15 when the valve 38 has shuttled to an open position, the chamber 15 is automatically relieved of further excess negative pressure therein.

Figures 6, 7:
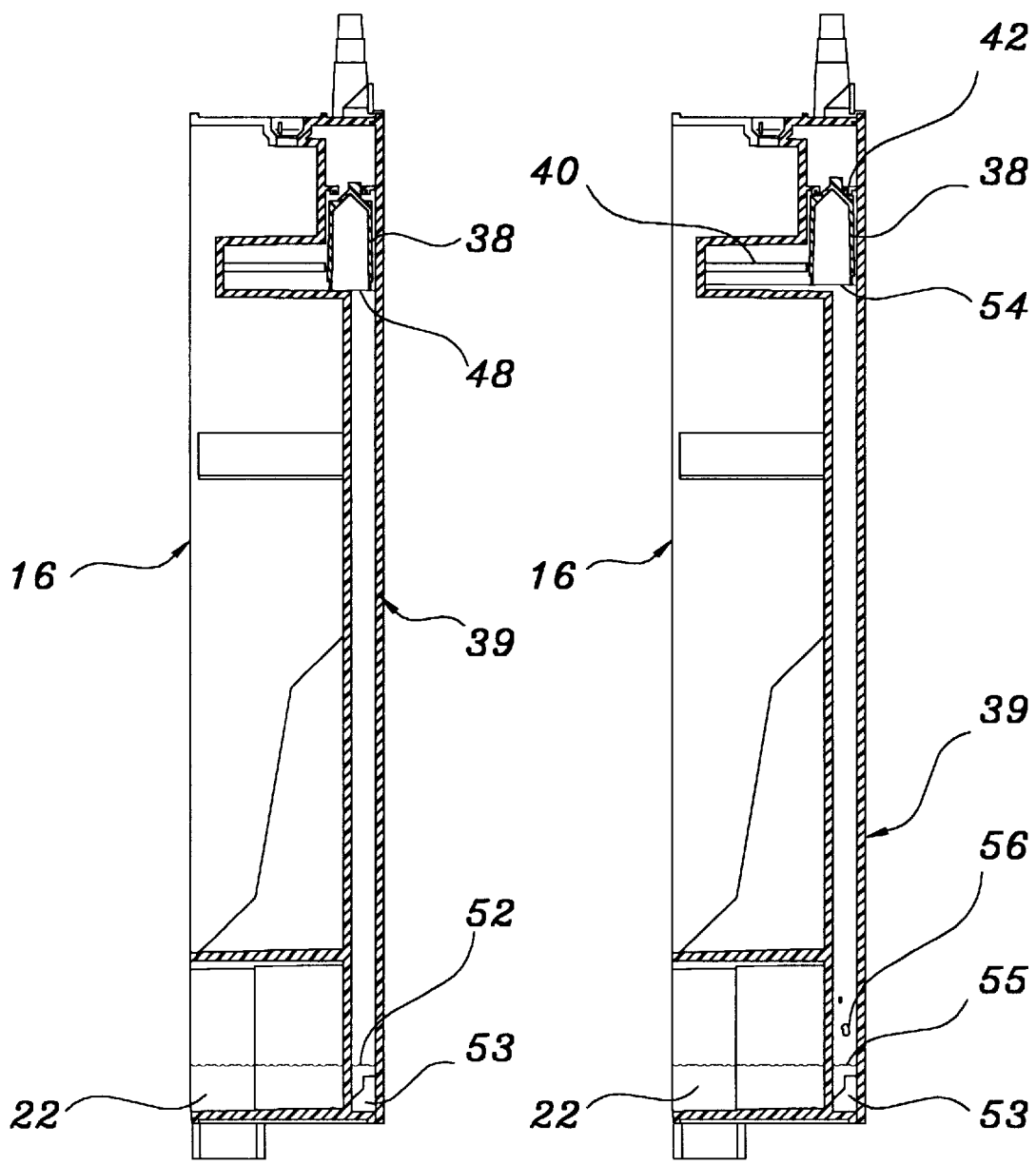
FIG. 6 is a cross section of the water seal chamber showing the shuttling action of the valve in the open position in accordance with the present invention.
FIG. 7 is a cross section of the water seal chamber showing the shuttling action of the valve while in the closed position in accordance with the present invention.

Referring now to FIGS. 6 and 7, a detailed description of the shuttling operation of valve 38 within the water seal chamber 16 will be explained. FIG. 6 shows valve 38 in the open position during low air flow conditions wherein water within the water seal 22 is forced up through column 39 due to the aforementioned slow increase in excess negative chamber within collection chamber 15. Water seal chamber 16 is configured in such a manner that a predetermined volume of water in water seal 22 is sufficient to completely fill up column 39 and engage valve 38 to valve seat 42 in sealing engagement therein, but not sufficient to maintain continuous engagement of valve 38. As seen in FIG. 6, the water has reached water level 48 prior to engagement of valve 38 to valve seat 42 while water in the water seal 22 has been correspondingly lowered to water level 52 just above seal opening 53. With reference to FIG. 7, if the slow increase in excess negative pressure continues the water will rise up column 39 until it reaches a water level 54. Once water level 54 has been reached valve 38 is placed in sealing engagement with valve seat 42, thereby closing valve 38 to fluid flow communication therethrough. When valve 38 is closed, water within water seal 22 will be further lowered to a water level 55 which places level 55 to a height equal to seal opening 53. By design, the height of water level 55 in relation to seal opening 53 causes air pockets or bubbles of air 56 to flow from the second arm 21 of water seal chamber 16 through seal opening 53 and up column 39. The rising air pocket 56 eventually displaces the water that closes off valve 38 because of the lack of hydraulic pressure support, thereby momentarily releasing it from its closed position.

Once valve 38 is released, rising water quickly replaces the air pocket 56 and valve 38 is again closed to fluid flow communication therethrough. This shuttling process alternates between the water that closes valve 38 and the air pocket 56 that opens it as long as the autotransfusion procedure or other of the aforementioned low air flow rate conditions persists. The shuttling action of valve 38 automatically maintains the desired negative pressure level inside collection chamber 15 until the procedure is terminated. In short, the present invention specifically tailors the volume of water in the water seal chamber 16 to a predetermined amount of water in the water seal 22, thereby generating air pockets 56 that alternate with the rising water to shuttle valve 38 between open and closed positions.

As mentioned briefly before, the slow rate of increase in the negative pressure inside collection chamber 15 is what causes the water to initially rise within water seal chamber 16. This slow excess negative pressure buildup can be generated by the operation of infusion pump 13 during autotransfusion, the drawing of a sample from a Y-site connector placed in fluid flow communication with infusion tubing 14 leading from collection chamber 15, or by utilizing a separate blood bag during autotransfusion as disclosed in U.S. Pat. No. 4,033,345 to Sorenson et al, whose teachings are herein incorporated by reference. Therefore, valve 38 is adapted to work in one of several operating environments where there is a slow rate of increase in the excess negative pressure inside the collection chamber 15 that causes a low air flow condition to arise which forces water in water seal 22 to slowly rise and migrate up column 39.

In the second mode of operation, valve 38 activates to close when an excessive negative pressure build up occurs nearly instantaneously such as in a high air flow rate generated by the patient taking a sudden and extended deep inspiration or "gasp". When a deep inspiration is performed, the patient has the potential of exerting a negative pressure of approximately –60 cm $H_2O$ inside collection chamber 15. This generates a high air flow rate condition moving in a direction of air flow D which results in a high pressure differential between the chamber 15 and the rest of CDU 11. In response to this condition, valve 38 rises to its closed position and remains closed until the patient releases the deep inspiration. This closed action occurs well before the water in column 39 can rise sufficiently to lift valve 38.

Valve 38 is adapted to close and open in response to any sudden inspiration by the patient. In the preferred embodiment, valve body 46 has a hollow-shaped configuration that is aerodynamically designed to engage valve seat 42 when the aforementioned high air flow condition is applied to the interior chamber 45. However, any suitable valve configuration that is adapted to close valve 38 when a high air flow condition is applied thereto in the direction of air flow D is felt to fall within the scope of the present invention.

A detailed operation of valve 38 during high air flow conditions will now be discussed. During convalescence when the patient takes an extended deep inspiration or "gasp" exercise, a high air flow condition within column 39 will exist in the direction of air flow D which enters valve chamber 40 and lifts valve body 46 into air-tight sealing engagement with valve seat 42. Once engaged, valve 38 will remain closed until the patient stops the deep inspiration which in turn releases and opens valve 38 from sealing engagement therein. This sealing engagement of valve 38 during high air flow conditions serves to maintain an equilibration in negative pressure between the collection chamber 15 and the patient's pleural cavity while aiding the patient to convalescence the pleural cavity.

The method of collecting and reinfusing fluids back to a patient using valve 38 as a safeguard in accordance with the present invention will now be discussed. The steps of collecting and reinfusing fluids to a patient first requires the practitioner to fill the water seal chamber 16 with approximately 40–42 cc of liquid. In the preferred embodiment, a pre-attached burette (not shown) having a volume in the range of 40–42 cc is located with CDU 11 so that the practitioner need only completely fill the burette and transfer the predetermined amount of liquid into the water seal chamber 16. In alternative embodiments, any suitable device that allows the practitioner to fill the correct amount of fluid and deposit or inject the same into water seal chamber 16 is felt to fall within the scope of the present invention. After filling water seal chamber 16, suction control chamber 17 is filled with liquid to a level adequate to maintain the proper negative pressure level inside CDU 11 required by the practitioner in a manner well known in the art.

Once the proper amount of negative pressure has been applied to inside of CDU 11 and the correct amount of liquid has been deposited in water seal chamber 16, infusion tubing 14 is attached to collection port 28 and a thoracic catheter (not shown), which has been inserted into the patient's pleural and mediastinal cavities, is attached to tubing 14. At that time, blood is collected in the collection chamber 15 by means of either gravity or suction drainage over a period of time. After a predetermined amount of blood has been collected, the practitioner may then order the autotransfusion procedure to commence. In order to establish the autotransfusion procedure, further infusion tubing 9 is used to place the outlet port 31 of collection chamber 15 in fluid flow communication with the inlet portion of infusion pump 13 while other tubing 8 is used to attach the outlet portion of pump 13 in fluid flow communication with the circulatory system of patient 12, thereby completing the assembly of system 10.

After completing assembly of system 10, a source of suction is applied to the suction port 18 and the infusion pump 13 is activated. Once the infusion pump 13 is activated, there will be a slow increase in negative pressure inside collection chamber 15 and a slow air flow rate condition will exist in the water seal chamber 16. Water from water seal 22 will slowly rise up column 39 until it engages valve 38, thereby starting the shuttling action of valve 38 between closed and open positions until such time as the infusion pump 14 is shut off.

Although particular embodiments of the invention have been shown, it is not intended that the invention be limited thereby, instead, the scope of the present invention is intended to be limited by only the appended claims.

We claim:

1. A system for the collection of fluids, comprising a closed vessel defining first, second and third intercommunicating chambers, said vessel being interposed between, and in fluid flow communication with, an infusion pump and a patient, said vessel having first, second and third openings for communication with the atmosphere, a vacuum source, and a fluid collection tube, respectively, a first water column and a water seal included in said first and second chambers, respectively, to define during normal operation first and second pressure differentials for establishing unidirectional flow from said first and third openings to said second opening while maintaining a desired sub-atmospheric pressure range in said third chamber, said second opening being in direct communication with a low pressure side of each of said first water column and said water seal, and an automatically releasing valve interposed between said second and third chambers for preventing fluid flow communication to said third chamber, the valve comprising, a valve chamber having a top and bottom portions, said top portion forming an aperture in fluid communication with said third chamber, said bottom portion being substantially open to said second chamber, a second water column, said second water column being interposed between said valve chamber and said water seal, a valve body disposed inside said valve chamber, said valve body defining a hollow interior chamber having a top section, said top section including a guide for facilitating engagement of said valve body to said aperture, a seal interposed between said valve body and said aperture, said seal closing off fluid flow communication between said second and third chambers when said valve body is engaged to said aperture, said valve body being shaped so that when, due to a negative pressure condition in said third chamber when said second water column rises to cause said valve body to be seated against said aperture in fluid-tight engagement thereto, an air pocket subsequently rises through said second water column and engages said valve body, thereby momentarily releasing said valve body from its engaged position in a shuttling action between said water column closing said valve and said air pocket releasing said valve until said negative pressure condition is eliminated.

2. The system according to claim 1, wherein said vessel has a fourth opening for draining fluids from said third chamber.

3. The system according to claim 1, wherein said valve closes said valve chamber from fluid flow communication therethrough in response to a high air flow rate condition in the third chamber.

4. The system according to claim 1, wherein said valve closes said valve chamber from fluid flow communication therethrough in response to an extended deep inspiration by the patient, said patient being in fluid flow communication with said closed vessel through a tube connected to said third opening.

5. The system according to claim 3, wherein said valve operates to maintain substantially the same pressure level in said third chamber as is present within the pleural cavity of said patient during a deep inspiration.

6. The system according to claim 4, wherein said valve operates to maintain substantially the same pressure level in said third chamber as is present within the pleural cavity of said patient during a deep inspiration.

7. The system according to claim 1, wherein said valve chamber further includes an accumulation chamber, said accumulation chamber adapted for receiving any excess water from said second water column as said valve is shuttling between open and closed states.

8. The system according to claim 1, wherein said water seal has a predetermined volume of liquid, said predetermined volume of liquid being insufficient to fill the volume of said second water column and said valve chamber during said overpressure condition, thereby generating said air pocket that rises up said second water column.

9. A flow rate sensitive valving mechanism for use in a system for the collection of fluids, the system including a closed vessel defining first, second and third intercommunicating chambers, the vessel being interposable between a pump and fluid being collected, the vessel having first, second and third openings in fluid flow communication with the atmosphere, a vacuum source, and a fluid collection tube, respectively, said flow rate sensitive valving mechanism comprising, a first column and a water seal positioned in the first and second chambers, respectively, said first column and water seal defining during normal operation, first and second pressure differentials for establishing unidirectional flow from said first and third openings to said second opening while maintaining a desired negative pressure level in said third chamber, said second opening being in direct communication with a low pressure side of each of said first column and said water seal, and a valve means for relieving excess negative pressure when there is a low air flow condition in said second chamber, said valve means operating in response solely due to changes in the fluid pressures exerted on the valve means, said operating being discontinuous, wherein said valve means repeatedly alternates between an open and a closed position until the excess negative pressure is relieved.

10. The system according to claim 9, wherein, said valve means is in fluid flow communication with a second column, said second column being interposed between said valve means and said water seal, said valve means is shaped so that when, due to the excess negative pressure condition in said third chamber when water in said second column rises to cause said valve means to close, an air pocket subsequently rises through said column and engages said valve means, thereby momentarily opening said valve means to fluid flow communication therethrough in a shuttling action between said column closing said valve means and said air pocket opening said valve means until said excess negative pressure condition is eliminated.

11. The system according to claim 9, wherein said closed vessel has a fourth opening for draining fluids from said third chamber.

12. The system according to claim 9, wherein said valve means closes in response to a high air flow rate condition in the third chamber.

13. The system according to claim 12, wherein said valve means operates to maintain substantially the same pressure level in said third chamber as is present within the pleural cavity of said patient during a deep inspiration.

14. The system according to claim 9, wherein said valve means further includes an accumulation chamber, said accumulation chamber adapted for receiving any excess water from said second column as said valve is shuttling between open and closed states.

15. The system according to claim 9, wherein said water seal has a predetermined volume of liquid, said predetermined volume of liquid being insufficient to fill the volume of said second column and said valve chamber during said overpressure condition, thereby generating said air pocket that rises up said second column.

16. A flow rate sensitive valving mechanism for use in a system for the collection of fluids, the system including a closed vessel defining first, second and third intercommunicating chambers, the vessel being interposable between a pump and fluid being collected, the vessel having first, second and third openings in fluid flow communication with atmosphere, a vacuum source, and a fluid collection tube, respectively, said flow rate sensitive valving mechanism comprising, a first column and a water seal positioned in the first and second chambers, respectively, said first column and water seal defining during normal operation, first and second pressure differentials for establishing unidirectional flow from said first and third openings to said second opening while maintaining a desired negative pressure level in said third chamber, said second opening being in direct communication with a low pressure side of each of said first column and said water seal, a valve means for relieving excess negative pressure when there is a slow air flow condition in said second chamber, said valve means being in fluid flow communication with a second column, said second column being interposed between said valve means and said water seal, said valve means shaped so that when, due to the excess negative pressure condition in said third chamber when water in said second column rises to cause said valve means to close, an air pocket subsequently rises through said second column and engages said valve means, thereby momentarily opening said valve means to fluid flow communication therethrough in a shuttling action between water in said second column closing said valve means and said air pocket opening said valve means until said excess negative pressure condition is eliminated.

17. The system according to claim 16, wherein said closed vessel has a fourth opening for draining fluids from said third chamber.

18. The system according to claim 16, wherein said valve means closes in response to a high air flow rate condition in the third chamber.

19. The system according to claim 18, wherein said valve means operates to maintain substantially the same pressure level in said third chamber as is present within the pleural cavity of said patient during a deep inspiration.

20. The system according to claim 16, wherein said valve means further includes an accumulation chamber, said accumulation chamber adapted for receiving any excess water from said second column as said valve is shuttling between open and closed positions.

21. The system according to claim 16, wherein said water seal has a predetermined volume of liquid, said predetermined volume of liquid being insufficient to fill the volume of said second column and said valve chamber during said overpressure condition, thereby generating said air pocket that rises up said second column.

22. A flow rate sensitive valving mechanism for use in a system for the collection of fluids, the system including a closed vessel defining first, second and third intercommunicating chambers, the vessel being interposable between a pump and fluid being collected, the vessel having first, second and third openings in fluid flow communication with atmosphere, a vacuum source, and a fluid collection tube, respectively, said flow rate sensitive valving mechanism comprising, a first column and a water seal positioned in the first and second chambers, respectively, said column and water seal defining during normal operation, first and second pressure differentials for establishing unidirectional flow from said first and third openings to said second opening while maintaining a desired negative pressure level in said third chamber, said second opening being in direct communication with a low pressure side of each of said first column and said water seal, a valve body positioned at a top portion of said second chamber and adapted for sealing engagement with a valve seat, said valve body being in fluid flow communication with a second column, said second column being interposed between said valve body and said water seal, said valve seat forming an aperture therethrough for fluid flow communication to said third chamber, whereby said valve body is shaped so that when, due to the excess negative pressure condition in said third chamber said second column rises to cause said valve body to close against said aperture in sealing engagement therein, an air pocket subsequently rises through said second column and engages said valve body, thereby momentarily opening said aperture to fluid flow communication therethrough in a shuttling action between said column closing said valve body and said air pocket opening said valve body until said excess negative pressure condition is eliminated.

23. The system according to claim 22, wherein said closed vessel has a fourth opening for draining fluids from said third chamber.

24. The system according to claim 22, wherein said valving mechanism closes in response to a high air flow rate condition in the third chamber.

25. The system according to claim 23, wherein said valving mechanism operates to maintain substantially the same pressure level in said third chamber as is present within the pleural cavity of said patient during a deep inspiration.

26. The system according to claim 22, wherein said valving mechanism further includes an accumulation chamber, said accumulation chamber adapted for receiving any excess water from said second column as said valve is shuttling between open and closed positions.

27. The system according to claim 22, wherein said water seal has a predetermined volume of liquid, said predetermined volume of liquid being insufficient to fill the volume of said second column and said valve chamber during said overpressure condition, thereby generating said air pocket that rises up said second column.

28. A method for collecting and reinfusing fluids to a patient using a closed vessel, the closed vessel defining first, second and third intercommunicating chambers, said vessel being interposed between, and in fluid flow communication with, an infusion pump and the patient, said vessel having first, second, and third openings for communication with atmosphere, a vacuum source, and a fluid collection tube, respectively, a first water column and a water seal included in said first and second chambers, respectively, to define during normal operation first and second pressure differentials for establishing unidirectional flow from said first and third openings to said second opening while maintaining a desired sub-atmospheric pressure range in said third chamber, said second opening being in direct communication with a low pressure side of each of said water column and said water seal, and a valve means for relieving excess negative pressure when there is a slow flow condition in said second chamber, a second water column interposed between said valve means and said water seal, which comprises the steps of:

a) filling a predetermined amount of liquid into the second chamber, said predetermined amount of liquid having a volume equal to said second water column;

b) filling a predetermined amount of liquid into the first water column;

c) placing said closed vessel in fluid flow communication with the pleural cavity of the patient and the pump;

d) applying a suction source to the second opening;

e) activating the pump, said pump causing a slow increase in negative pressure inside the third chamber in such a manner that said liquid in the second chamber rises up the second water column and engages and closes the valve means, said valve means subsequently opening after all the liquid in the water seal has filled the entire volume of the second water column and an air pocket is forced up the second water column due to insufficient volume of liquid in the water seal where it contacts and opens said valve means in a shuttling action between open and closed positions until said slow increase in negative pressure is eliminated.

29. The method according to claim 28, wherein said slow increase in negative pressure occurs inside said third chamber and is caused by operation of a pump reinfusing liquids back to the patient.

30. The method according to claim 28, wherein said slow increase in negative pressure occurs inside said third chamber and is caused by a taking a sample of liquid using a sampling means.

31. The method according to claim 30, wherein said sampling means is a syringe.

32. The method according to claim 28, wherein said slow increase in negative pressure occurs inside said third chamber and is caused by atmospheric changes outside the closed vessel.

33. The method according to claim 28, wherein said slow increase in negative pressure occurs inside said third chamber and is caused by physiological changes associated with the patient.

34. The method according to claim 28, wherein said slow increase in negative pressure occurs inside said third chamber and is caused by interposing a separate collection vessel in fluid flow communication between said pump and said closed vessel.

35. A system for the collection of body fluids from a patient, said closed vessel defining first, second and third intercommunicating chambers, said vessel being interposed between, and in fluid flow communication with, an infusion pump and the patient, said vessel having first, second and third openings for communication with atmosphere, a vacuum source, and a fluid collection tube, respectively, a first water column and a water seal included in said first and second chambers, respectively, to define during normal operation first and second pressure differentials for establishing unidirectional flow from said first and third openings to said second opening while maintaining a desired negative pressure level in said third chamber, said second opening being in direct communication with a low pressure side of each of said first water column and said water seal, and a valve means for relieving excess negative pressure, wherein when a slow air flow condition exists in said second chamber said valve means is shaped so that when, due to the excess negative pressure condition in said third chamber when said second column rises to cause said valve means to close, an air pocket subsequently rises through said second water column and engages said valve means, thereby momentarily opening said valve means to fluid flow communication therethrough in a shuttling action between said second water column closing said valve means and said air pocket opening said valve means until said excess negative pressure condition is eliminated, and wherein when a high flow rate condition exists in said third chamber said valve means closes in response to a said high air flow condition.

36. The system according to claim 35, wherein said closed vessel has a fourth opening for draining fluid from said third chamber.

37. The system according to claim 35, wherein said valve means closes in response to an extended deep inspiration by the patient.

38. The system according to claim 35, wherein said valve means operates to maintain substantially the same pressure level in said third chamber as is present within the pleural cavity of said patient during high flow rate conditions.

39. The system according to claim 35, wherein said second chamber further includes a second water column, said second water column being interposed between said valve means and said water seal.

40. The system according to claim 39, wherein said water seal has a predetermined volume of liquid, said predetermined volume of liquid being insufficient to fill the volume of said second water column and said valve chamber during said overpressure condition.

* * * * *